(12) United States Patent
Nedwed et al.

(10) Patent No.: US 9,810,522 B2
(45) Date of Patent: Nov. 7, 2017

(54) METHOD AND SYSTEM FOR HYDROCARBON RELEASE MANAGEMENT

(71) Applicants: Timothy J. Nedwed, Houston, TX (US); David A. Palandro, The Woodlands, TX (US)

(72) Inventors: Timothy J. Nedwed, Houston, TX (US); David A. Palandro, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 202 days.

(21) Appl. No.: 14/385,473

(22) PCT Filed: Mar. 19, 2013

(86) PCT No.: PCT/US2013/032994
§ 371 (c)(1),
(2) Date: Sep. 15, 2014

(87) PCT Pub. No.: WO2013/162790
PCT Pub. Date: Oct. 31, 2013

(65) Prior Publication Data
US 2015/0047420 A1    Feb. 19, 2015

Related U.S. Application Data

(60) Provisional application No. 61/638,190, filed on Apr. 25, 2012.

(51) Int. Cl.
*G01N 13/00* (2006.01)
*G01B 11/06* (2006.01)
*E02B 15/04* (2006.01)
*G01B 11/02* (2006.01)
*G01C 13/00* (2006.01)
(Continued)

(52) U.S. Cl.
CPC ............ *G01B 11/06* (2013.01); *E02B 15/04* (2013.01); *G01B 5/06* (2013.01); *G01B 11/022* (2013.01); *G01C 13/00* (2013.01); *G01N 11/12* (2013.01); *G01N 33/1886* (2013.01); *G01N 33/28* (2013.01); *G01B 21/08* (2013.01); *G01C 11/04* (2013.01)

(58) Field of Classification Search
CPC .... G01N 33/1833; G01N 33/26; G01N 33/28; G01B 5/06; G01B 11/022; G01B 11/06; G01B 21/08; G01C 13/00; G01C 11/04; E02B 15/00; E02B 15/04; G01L 35/06
USPC ......................................... 73/64.55; 210/922
See application file for complete search history.

(56) References Cited

U.S. PATENT DOCUMENTS 3,885,418 A     5/1975   Kriebel
4,563,674 A *   1/1986   Kobayashi ......... B01D 17/0214
                                                    210/315

(Continued)

*Primary Examiner* — Benjamin Schmitt
(74) *Attorney, Agent, or Firm* — ExxonMobil Upstream Research Company—Law Department

(57) ABSTRACT

Method and system is described to enhance operations for managing the hydrocarbon release. The system utilizes an airborne detection device equipped with measurement components and communication components. The system may utilize various measurement techniques to determine the thickness of the oil slick. This remote detection method may provide a dedicated airborne detection device for each response vessel and that can identify the location and thickness of the oil slick.

26 Claims, 10 Drawing Sheets

(51) Int. Cl.
*G01B 5/06* (2006.01)
*G01N 11/12* (2006.01)
*G01N 33/18* (2006.01)
*G01N 33/28* (2006.01)
G01C 11/04 (2006.01)
G01B 21/08 (2006.01)

(56) References Cited

U.S. PATENT DOCUMENTS

| | | |
|---|---|---|
| 5,045,216 A | 9/1991 | Eller |
| 5,381,442 A | 1/1995 | Brown et al. |
| 5,481,904 A * | 1/1996 | Fleck, Sr. ................ G01N 1/12 340/605 |
| 2004/0257264 A1 * | 12/2004 | Moeller-Jensen . G01N 33/1833 342/52 |
| 2009/0039255 A1 * | 2/2009 | Andrews ................ G01N 21/35 250/301 |
| 2009/0069956 A1 | 3/2009 | Taya et al. |
| 2011/0060551 A1 | 3/2011 | Elhajj |
| 2015/0253126 A1 * | 9/2015 | Palandro ................ G01B 11/06 348/135 |

\* cited by examiner

METHOD AND SYSTEM FOR HYDROCARBON RELEASE MANAGEMENT

CROSS-REFERENCE TO RELATED APPLICATION

This application is the National Stage of International Application No. PCT/US2013/032994, filed Mar. 19, 2013, which claims the benefit of U.S. Provisional Patent Application 61/638,190, filed Apr. 25, 2012, entitled METHOD AND SYSTEM FOR HYDROCARBON RELEASE MANAGEMENT, the entirety of which is incorporated by reference herein.

FIELD OF THE INVENTION

This invention relates generally to the field of hydrocarbon operations. Specifically, the invention relates to operations for managing oil releases, which utilize one or more airborne devices.

BACKGROUND OF THE INVENTION

In the oil and gas industry, hydrocarbons are accessed via a wellbore to provide a fluid flow path to a processing facility. Some of these hydrocarbon resources are located under bodies of water, such as lakes, seas, bays, rivers and/or oceans, while others are located at onshore locations. To transfer hydrocarbons from such locations, a pipeline and/or one or more different vessels (e.g., ship or tanker trucks) may be utilized through various segments from the wellbore and the processing facility.

Additionally, hydrocarbons may be transferred from a production region to another region for consumption/processing into hydrocarbon-based products or from one hydrocarbon storage location to another. Transfer of hydrocarbons between such locations often requires one or more different vessels and routes over bodies of water, such as lakes, seas, bays, rivers and/or oceans.

Offshore leaks and/or spills may be problematic due to the hydrocarbons being released into a body of water. Typically, the hydrocarbons may form a slick on the surface of the water, which may be referred to as an oil slick. Various response techniques may be utilized to manage the oil slick. For instance, chemicals may be added to the oil slick and mixed with the oil slick to break apart the hydrocarbons. In other situations, the oil slick may be ignited to burn off the oil slick or mechanical recovery may be utilized to capture the hydrocarbons.

In managing an oil slick, various factors (e.g., spatial distribution and thickness) should be considered as part of the assessment. The spatial distribution and thickness are useful in estimating the volume of hydrocarbons present in the oil slick. For example, conventional practice for marine oil spills is that 90% of the oil is located in 10% of the area as most of the slick is very thin. Determining the oil slick thickness is useful for oil spill response for many of the different response techniques. For example, mechanical recovery and in situ burning are more efficient on thick oil slick. Also, dispersant dosage requirements change based on the slick thickness.

While the spatial distribution is typically estimated from visual inspection, conventional approaches do not adequately estimate the thickness of the oil slick. For example, conventional approaches typically utilize aircraft to determine the location of an oil slick for marine vessels. With this approach, a trained spotter or an instrument that detects an electromagnetic radiation signal from the slick is located in an airplane and in communication with response vessels. The challenge is that visual and electromagnetic radiation indicators are unable to distinguish oil thicker than about 0.1 mm.

An additional challenge is that for a large spill, each spotter is responsible for multiple response vessels, which requires the spotter in the plane to divide attention between the different response vessels. This approach has proven inefficient because identifying oil slicks from a marine response vessel combined with their dynamic nature at sea requires the spotter plane to focus on a single marine vessel until it is directly adjacent to the oil slick because it is very challenging to identify oil slicks that are more than a few tens of meters away from vessels at sea. Unfortunately, spotter planes are often unable to dedicate attention to a single vessel for the time required to efficiently guide it onto a slick. Accordingly, conventional methods fail to provide simple remote identification and effective estimation of the thickness of marine oil slicks.

As the management of hydrocarbon leaks and spills is a time consuming operation, a need exists to enhance operations to manage hydrocarbon releases with enhanced methods and systems. In particular, a need exists for a remote detection method that is dedicated to each response vessel and that can identify the thickness of the oil slick.

SUMMARY OF THE INVENTION

In one embodiment, a method for managing an oil release with one or more airborne devices is described. The method may comprise deploying a marine vessel having an airborne detection device to a location in a body of water near an oil slick; hovering the airborne detection device above the oil slick; measuring thickness of the oil slick at the location; and transmitting a signal associated with the thickness of the oil slick to a command unit. Further, the method may include determining a response technique based at least partially on the thickness of the oil slick.

In one or more embodiment, a hydrocarbon release management system is described. The system comprises a command unit; and an airborne detection device in communication with the command unit and having a propulsion component, a communication component and a measurement component, wherein the propulsion component is configured to maneuver the airborne detection device, the measurement component is configured to measure the thickness of the oil slick and the communication component is configured to communicate signals associated with the measured thickness to the command unit. The airborne detection device may be configured to be controlled via remote control communications.

In one more embodiments, the method or system may include additional aspects. For example, the method may include programming the airborne detection device to be able to communication with the command unit prior to hovering the airborne detection device. The airborne detection device may further include a power component that is configured to provide power to one or more of the measurement component and the communication component. The communication component may be configured to transmit to the command unit via one or more of wireless communication hardware and cellular communication hardware. Further, the measurement component may comprise a camera attached to a retractable line, wherein the camera is a high definition camera. Also, the measurement component may comprise an object attached to a retractable line, which may be one of a Secchi-type disk, weight, accelerometer and conductivity probe. Further still, the measurement component may include a sample tube attached to a retractable line and a camera configured to image the sample tube.

In one or more embodiments, the measuring thickness of the oil slick may include various techniques, such as (i) using down wash from the airborne detection device to clear the area within the oil slick, and recording a clearing time. Another technique may include dropping a Secchi-type disk into the oil slick, measuring a time period for the helicopter cameras to lose sight of the disk from the initial dropping of the Secchi-type disk; (ii) dropping an accelerometer into the oil slick to measure the amount of time required for the accelerometer to pass through the oil slick; and retracting the accelerometer out of the oil slick; (iii) dropping a small visible weight into the oil slick; recording the amount of time for the small visible weight to pass through the oil slick based on a loss of visibility, and retracting the small visible weight out of the oil slick; (iv) lowering a sample tubes until the sample tube extends from above the oil slick to a location below the oil slick, closing the ends of the sample tube, retracting the sample tube from the oil slick, and obtaining an image of the filled sample tube; (v) lowering an imaging camera into the oil slick to photograph a profile of the air-oil-water interfaces, capturing the image and retracting the imaging camera out of the oil slick; (vi) lowering a conductivity probe into the oil slick and partially through the oil slick to the water beneath the oil slick, measuring resistance of the oil and water phases, and retracting the conductivity probe. The method may also include receiving the signal at the command unit; extracting a measured thickness image from the signal and displaying the measured thickness image on a monitor or receiving the signal; extracting measured data from the signal, and comparing the measured data to a table to determine the thickness of the oil slick.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION OF THE PREFERRED EMBODIMENTS

Figure 1:
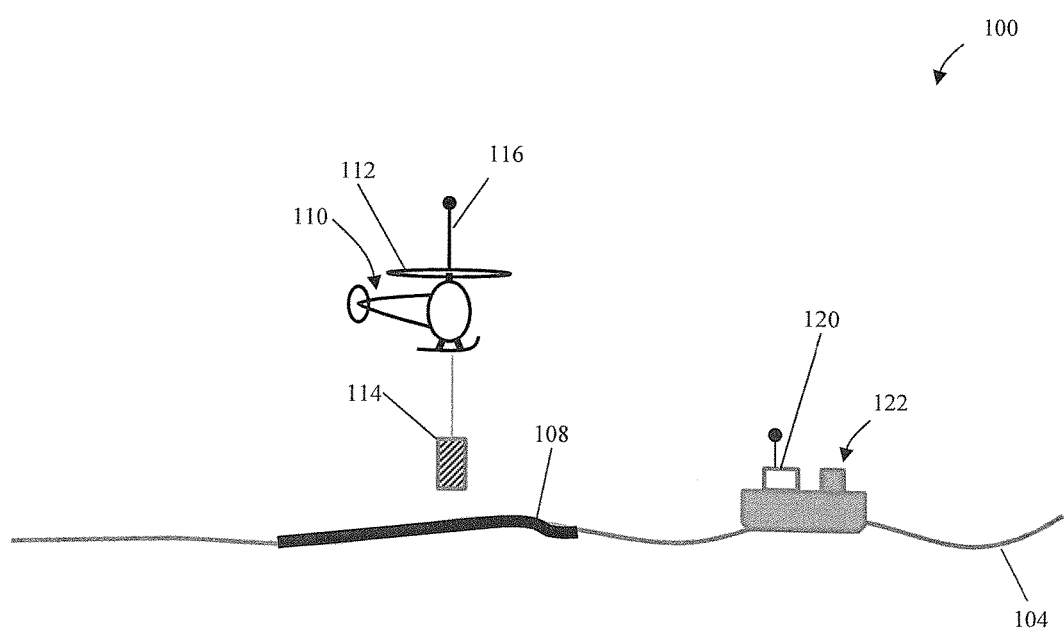
FIG. 1 is a diagram of an airborne hydrocarbon release management system in accordance with an exemplary embodiment of the present techniques.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

The present disclosure describes an airborne hydrocarbon detection system and method. With this airborne hydrocarbon detection system, one or more response vessels may include one or more airborne detection devices that include propulsion components and measurement components. The airborne detection devices may be manually controlled or may be automated or combinations thereof. Further, the airborne detection devices may also include communication components to enhance operation of the system. As an exemplary embodiment, the airborne detection device may be a remote-controlled helicopter. The remote-controlled helicopter may include a high-definition camera and an infrared camera for locating oil slicks and one or more of several measurement components for determining the thickness of the oil slick.

In certain embodiments, the system and method may include one or more different measurement components utilized to determine the thickness of the oil slick. Each of these measurement components may include different techniques to obtain measurements associated with the thickness of the oil slick. These techniques may include using the down wash of the airborne detection device to clear the area within the oil slick, recording the time period to clear the area and comparing the clearing time to predetermined tables that correlate clearing time to oil slick thickness. Another technique may include dropping a single-use Secchi-type disk (or similarly visible object) into the oil slick, measuring the amount of time required for the helicopter cameras to lose sight of the disk, and comparing the time to predetermined tables that correlate this time to oil slick thickness. Yet another technique includes dropping an accelerometer located on a retractable line into the oil slick, measuring the amount of time required for the accelerometer to pass through the oil slick, and comparing the time to predetermined tables that correlate this time to slick thickness. The accelerometer is used multiple times by repeatedly deploying and retracting via the retractable line. In another similar technique, a small visible weight is dropped into the oil slick, the amount of time for it to pass through the oil slick based on the loss of visibility is measured, the object is retracted back out of the oil slick and the time to loss of visibility is compared to predetermined tables that correlate this time to slick thickness. In yet another technique, a sample tube open at both ends is dropped until it extends from above the oil slick to a location below the oil slick, the ends of the sample tube are then closed via a remote actuation device, the tube is retracted from the oil slick and an image of the tube may be obtained to directly determine slick thickness. Further, another technique may include dropping an imaging camera into the oil slick to photograph a profile of the air-oil-water interfaces to directly determine slick thickness. The camera is located on a retractable line allowing rapid image of multiple areas of a slick and/or multiple slicks. A conductivity probe located on a retractable line to measure the resistance of the water and oil slick phases to determine slicks thickness. Various aspects of the present techniques are described further in FIGS. 1 to 10.

FIG. 1 is a diagram of an airborne hydrocarbon release management system 100 in accordance with an exemplary embodiment of the present techniques. The airborne hydrocarbon release management system 100 may include one or more airborne detection devices, such as airborne detection device 110, which are in communication with a command unit 120, which is shown disposed on a ship 122. The airborne detection devices and the ship 122 may be disposed in a body of water 104 and the airborne detection devices may be deployed to determine the location of an oil slick 108 and to determine the thickness of the oil slick 108 at various locations.

Each airborne detection device may include propulsion components 112 to maintain the airborne detection device above the water 104 and measurement components 114 that are utilized to measure the spatial distribution and the thickness of the oil slick. In addition, the airborne detection device may optionally include a communication component 116 that is configured to communicate with the command unit 120 and calculate the thickness of the oil slick. The propulsion components 112 may be utilized to both maneuver the airborne detection device 110 and power the measurement components 114 and communication component 116. These power components may include a battery and/or solar powered equipment. The different components or modules may be powered from the power component or may include separate power sources for each of the respective components or modules. Also, the different components and modules may also utilize a separate power source as a redundant power supply in certain embodiments.

The measurement components 114 may include various different measurement components to perform one or more of the measurement techniques. These may include one or more HD cameras, IR cameras, wench components (to lower and retract thickness measurement components) and other suitable equipment. Thickness measurements components may include one or more of multiple single-use Secchi discs, a visible weight mounted on a retractable line, open ended sample tubes mounted on a retractable line, a profiling camera mounted on a retractable line, and/or a conductivity probe mounted on a retractable line.

The communication components 116 may include communication equipment that is utilized with one or more antennas to communicate with one or more of other airborne detection devices, internal components or modules, and/or the command unit 120. The communication equipment may utilize technologies, such as radio, cellular, wireless, microwave or satellite communication hardware and software. Also, the communication equipment may include and utilize any of a variety of known protocols to manage the exchange of information (e.g., Ethernet, TCP/IP, and the like). The communication equipment utilized may depend on the specific deployment locations and configuration. For example, if two or more airborne detection devices are located in close proximate to each other, one airborne detection device may include satellite communication equipment along with radio or wireless communication equipment, while the other airborne detection devices may include only radio or wireless communication equipment. In this manner, the airborne detection device with the satellite communication equipment may handle communication to the command unit 120 for the other airborne detection devices.

Figure 2:
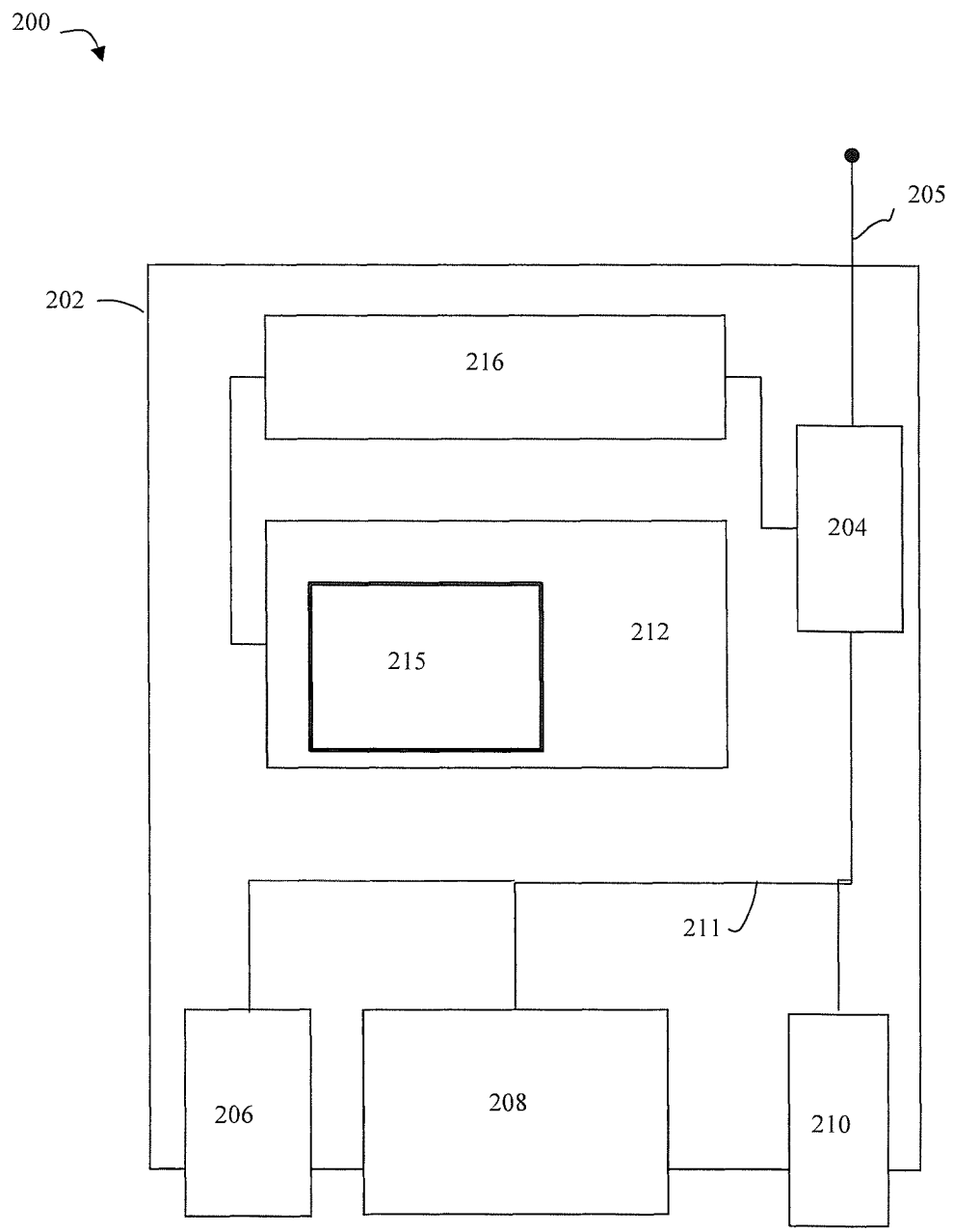
FIG. 2 is a diagram of an airborne monitoring device in accordance with an exemplary embodiment of the present techniques.

FIG. 2 is an exemplary airborne detection device 200, which may be one embodiment of the airborne detection device 110 of FIG. 1. In this FIG. 2, the exemplary airborne detection device 200 includes a housing 202 that encloses one or more of a communication component 204 and associated antenna 205, a high definition (HD) camera 206, a thickness measurement component 208, an infrared (IR) camera 210, a power component 212 and a propulsion component 216. The modules and components are provided power from the power component 212 via power distribution lines (not shown). Similarly, the different modules and components may communicate with each other via communication lines 211. This embodiment utilizes central power and communication lines to manage the operation in an efficient manner.

To operate, the power component 212 may be utilized to supply power to the propulsion component 216. Further, the power component 212 may provide power to the communication component 204, the high definition (HD) camera 206, the thickness measurement component 208, and the infrared (IR) camera 210. In this embodiment, the power component 212 includes batteries 215 and a motor (not shown). The batteries 215 may provide power via the power distribution lines, which may include one or more cables, as an example. The motor may turn fuel into power, which may be used to power the modules and components and also to recharge the batteries 215.

The communication component 204 is utilized to exchange information between the different modules and components and/or the command unit via the communication lines 211 and the communication antenna 205. The communication component 204 may utilize the communication lines 211 to handle the exchange of information, such as measured data, status indications or other notifications, between the modules, such as the high definition (HD) camera 206, the thickness measurement component 208, the infrared (IR) camera 210, the power component 212 and the propulsion component 216. The communication lines 211 may include a bus, Ethernet cable, fiber optics or other suitable physical connection. In an alternative embodiment, the communication between modules may be via a wireless connection. Similarly, the communication protocol may be any protocol known to those skilled in the art.

To monitor the oil slick, the high definition (HD) camera 206, the thickness measurement component 208, and the infrared (IR) camera 210 may be utilized to measure spatial distribution or thickness of the oil slick. Examples of different measurement components and the associated techniques to obtain measurements are noted further below. As an example, the thickness measurement component 208 may include a loading component to load a Secchi-type disk, weight or similarly visible object, a wench component to raise and lower a camera, sample tube, weight, object, accelerometer, conductivity probe and the like. The cameras 206 and 210 may be used with the measurement component 208 to assist in imaging, measuring or determining the oil slick thickness. The various measurement techniques are described further in FIGS. 3 to 9.

Referring back to FIG. 1, the command unit 120 may be utilized as a central location to manage the one or more airborne detection devices. The command unit 120 may include power components, communication components and/or management components. The command unit 120 may be disposed on a vessel, such as ship 122, to facilitate communication and interaction with the airborne detection devices. However, other embodiments may include the command unit 120 being located at an onshore location, on a platform, or even other remote location.

Similar to the airborne detection device 110, the power components may include a battery and/or solar powered equipment. Further, the power components for the command unit 120 may also include turbines and/or engines. That is, the command unit 120 may be disposed on a vessel, such as ship 122, which may include motors that supply power to equipment on the ship 122.

The communication components may include communication equipment that is utilized with one or more antenna to communicate with one or more of other airborne detection devices and other operation centers. The communication equipment may utilize technologies, such as radio, cellular, wireless, microwave or satellite communication hardware and software. Also, the command unit may utilize Ethernet communications, such as local area networks or wide area networks.

The management components may include different modules, which may include hardware, sets of instructions stored in memory and configured to be accessed by a processor to execute the set of instructions, or a combination of both. These modules may include display and imaging module that present the images or visible indications to an operator, and modules configured to determine the thickness of the oil slick. Persons skilled in the technical field will readily recognize that in practical applications of the disclosed methodology, it is partially performed on a computer, typically a suitably programmed digital computer. Further, some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing" or "computing", "calculating", "determining", "displaying", "copying," "producing," "storing," "adding," "applying," "executing," "maintaining," "updating," "creating," "constructing" "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general-purpose computer selectively activated or reconfigured by a computer program stored in the computer (e.g., one or more sets of instructions). Such a computer program may be stored in a computer readable medium. A computer-readable medium includes any mechanism for storing or transmitting information in a form readable by a machine (e.g., a computer). For example, but not limited to, a computer-readable (e.g., machine-readable) medium includes a machine (e.g., a computer) readable storage medium (e.g., read only memory ("ROM"), random access memory ("RAM"), magnetic disk storage media, optical storage media, flash memory devices, etc.), and a machine (e.g., computer) readable transmission medium (electrical, optical, acoustical or other form of propagated signals (e.g., carrier waves, infrared signals, digital signals, etc.)).

Furthermore, as will be apparent to one of ordinary skill in the relevant art, the modules, features, attributes, methodologies, and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present invention is in no way limited to implementation in any specific operating system or environment.

Further, one or more embodiments may include methods that are performed by executing one or more sets of instructions to perform modeling enhancements in various stages. For example, the method may include executing one or more sets of instructions to perform comparisons between measured time or indications along with transmitting data between modules and/or components.

As an example, a computer system may be utilized and configured to implement on or more of the present aspects. The computer system may include a processor; memory in communication with the processor; and a set of instructions stored on the memory and accessible by the processor, wherein the set of instructions, when executed, are configured to: receive the transmitted signal from the airborne detection device; determine the thickness of the oil slick based on the transmitted signal; and provide a visible indication of the thickness of the oil slick based on the determination. Further, the determination of the thickness of the oil slick based on the transmitted signal may comprise a set of instructions, when executed, configured to: compare a measured time to estimated time table; and display on a monitor the thickness of the oil slick based on this comparison. Further, the determination of the thickness of the oil slick based on the transmitted signal may comprise a set of instructions, when executed, configured to: compare a measured accelerometer data to estimated accelerometer data table; and display on a monitor the thickness of the oil slick based on this comparison. Further still, the determination of the thickness of the oil slick based on the transmitted signal may comprise a set of instructions, when executed, configured to display the image on a monitor to determine the thickness of the oil slick based on this comparison. In addition, the determination of the thickness of the oil slick based on the transmitted signal may comprise a set of instructions, when executed, configured to: compare a measured resistance to an estimated resistance table; and display on a monitor the thickness of the oil slick based on this comparison.

In one or more embodiments, the command unit may include a set of instructions stored on the memory and accessible by the processor, wherein the set of instructions, when executed, are configured to provide one or more of a visual indication and audible notification associated with the thickness of the oil slick. Also, the command unit may include a set of instructions stored on the memory and accessible by the processor, wherein the set of instructions, when executed, are configured to store the thickness of the oil slick at the specific location.

Figure 3:
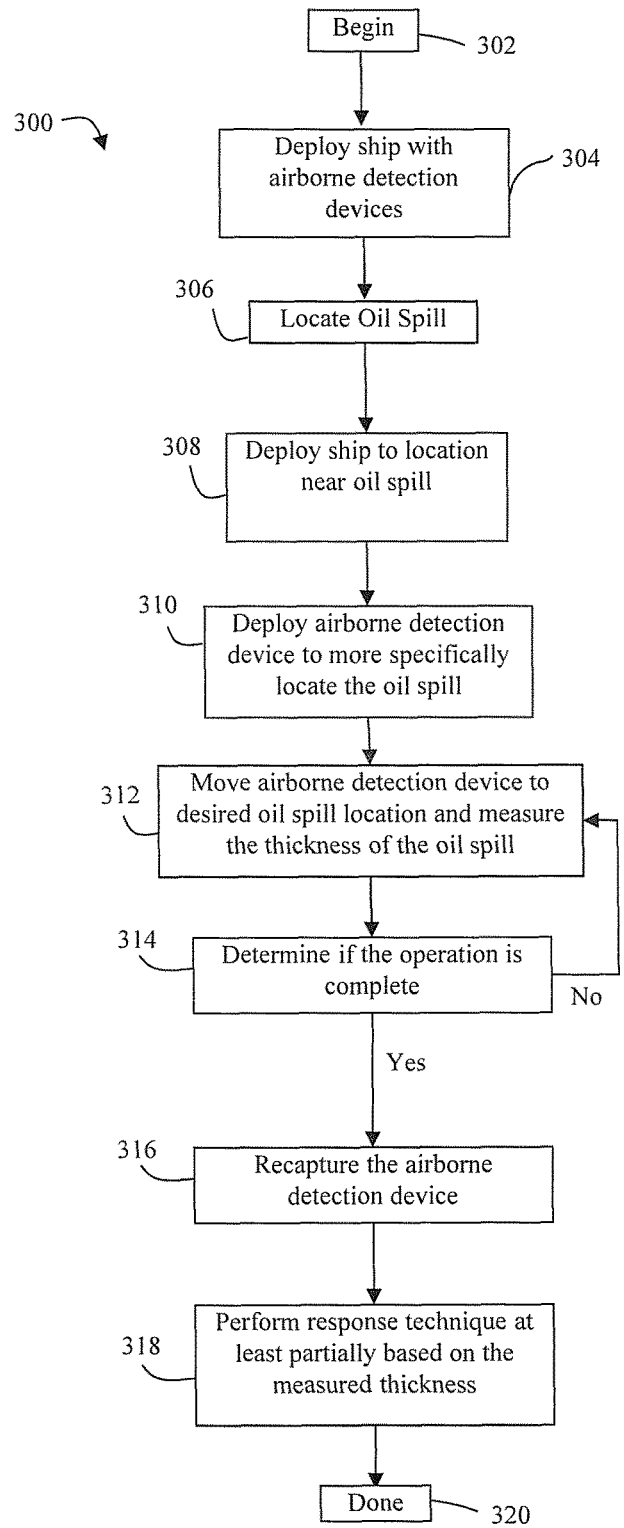
FIG. 3 is a flow chart for performing airborne oil release management in accordance with an exemplary embodiment of the present techniques.

FIG. 3 is a flow chart 300 for performing airborne oil release management in accordance with an exemplary embodiment of the present techniques. This flow chart 300 includes a preparation and deployment stage, which includes blocks 302, 304, 306 and 308, followed by a detection and measurement stage, which includes blocks 310, 312, 314 and 316, and followed by a response stage, which includes blocks 318 and 320.

The process begins with the preparation and deployment stage, which prepares the equipment and deploys the equipment to the oil spill location. The process begins at block 302. Then, at block 304, the ship with one or more airborne detection devices is deployed. The deployment of the ship may include fueling the ship, loading the one or more airborne detection devices onto the ship and moving the ship from port. The deployment may also include selecting the measurement components to be utilized with the airborne detection device. Either prior to or once the ship is deployed, the oil spill may be located, as shown in block 306. Locating the oil spill may include areal reconnaissance or identification from marine vessels, platforms or other suitable means. Then, the ship is deployed to a location near the oil spill, as shown in block 308. This location may be communicated to the ship. The deployment of the ship may include transporting the airborne detection devices to a location near that indicated in the communication.

After the preparation and deployment stage, the monitoring and operation stage is performed, as noted in blocks 310, 312, 314 and 316. In block 310, the airborne detection device is deployed from the ship to determine the location of the oil spill. This may involve controlling the airborne detection device to move above the oil slick to a specific location. That is, the airborne detection device, which may be a remote controlled helicopter, as an example, may fly to a location above the oil slick. Then, the thickness of the oil slick is measured. The airborne detection device may be configured to transmit information within a set time window (e.g., every 10 seconds, 60 seconds, 5 minutes, or even 10 minutes), transmit information when polled by the command unit, or transmit information when after each measurement has been collected.

The measurement of the oil slick may include hovering the airborne detection device over a specific location in the oil slick and performing one or more of the measurement techniques. These measurement techniques may include one or more different measurement components utilized with the airborne detection device to determine the thickness of the oil slick. These techniques may include using the down wash of the airborne detection device to clear the area within the oil slick, recording the time period to clear the area and comparing the clearing time to predetermined tables that correlate clearing time to oil slick thickness. Another technique may include dropping a single-use Secchi-type disk (or similarly visible object) into the oil slick, measure the amount of time required for the helicopter cameras to lose sight of the disk, and compare the time to predetermined tables that correlate this time to oil slick thickness. In yet another technique, an accelerometer is dropped into the oil slick to measure the amount of time required for the accelerometer to pass through the oil slick, retracted via a line out of the oil slick, and the time is compared to predetermined tables that correlate this time to slick thickness. In another similar technique, a small visible weight is dropped into the oil slick, the amount of time for it to pass through the oil slick based on the loss of visibility is measured, the object is retracted back out of the oil slick and the time to pass through the slick is compared to predetermined tables that correlate this time to slick thickness. In yet another technique, an open-ended sample tubes is dropped until it extends from above the oil slick to a location below the oil slick, the sample tube ends are closed via a remote actuating device, the tube is retracted from the oil slick and an image of the tube may be obtained to directly determine slick thickness. Further, another technique may include dropping an imaging camera via a retractable line into the oil slick to photograph a profile of the air-oil-water interfaces, the camera captures the image allowing direct determination of oil slick thickness. In yet another technique, a conductivity probe is deployed via a retractable line into the oil slick to measure the resistance of the oil and water phases. This resistance is compared to predetermined tables that correlate resistance to slick thickness. Further exemplary embodiments of the measurement techniques are described further in FIGS. 4 to 10.

Once the measurement has been obtained, a determination is made whether the operation is complete, as shown in block 314. If the operation is not complete, the airborne detection device may be deployed to another location to measure the thickness of the oil slick, as shown in block 310. However, if the operation is complete, then the airborne detection device is recaptured, as shown in block 316.

Once the detection and measurement stage is complete, the response stage, which includes blocks 318 and 320, may be performed. At block 318, the response techniques may be performed based at least partially on the measured thickness. That is, with the thickness and the spatial distribution, the response team may manage the oil slick in an efficient and enhanced manner. For instance, the response team may prioritize treating the thicker slicks or slick portions earlier and thinner portions later to increase response efficiency. Thick slicks may be greater than 0.1 mm, 0.5 mm, 1.0 mm, 2.0 mm, or more.

As noted above, FIGS. 4 to 10 are flow charts for different methods of performing measurements with an airborne detection device in accordance with an exemplary embodiment of the present techniques. For simplicity, each of these flow charts describes the use of a remote controlled helicopter as the airborne detection device. The helicopter may be remotely controlled by an operator on a marine response vessel that is positioned near the oil spill. This helicopter may also include high definition (HD) and inferred (IR) cameras that transmit these signals to a command unit on the oil spill response vessel. As may be appreciated, the methods may begin by flying the helicopter from the deck of the vessel to a position above the vessel. This initial flight may be utilized to test the communications with the helicopter. Then, the helicopter may be utilized to locate the oil slick, which may provide a spatial distribution of the oil slick. The oil slick may be identified by the HD and ID cameras based on either visual cues from the HD camera or infrared cues from the IR camera. It is known by those practiced in the art that oil slicks on a water surface tend to have different temperatures than the water surface itself. These temperature differences are readily detectable via an IR camera. Then, the different respective thickness measurement methods, which are described below, are implemented.

Figure 4:
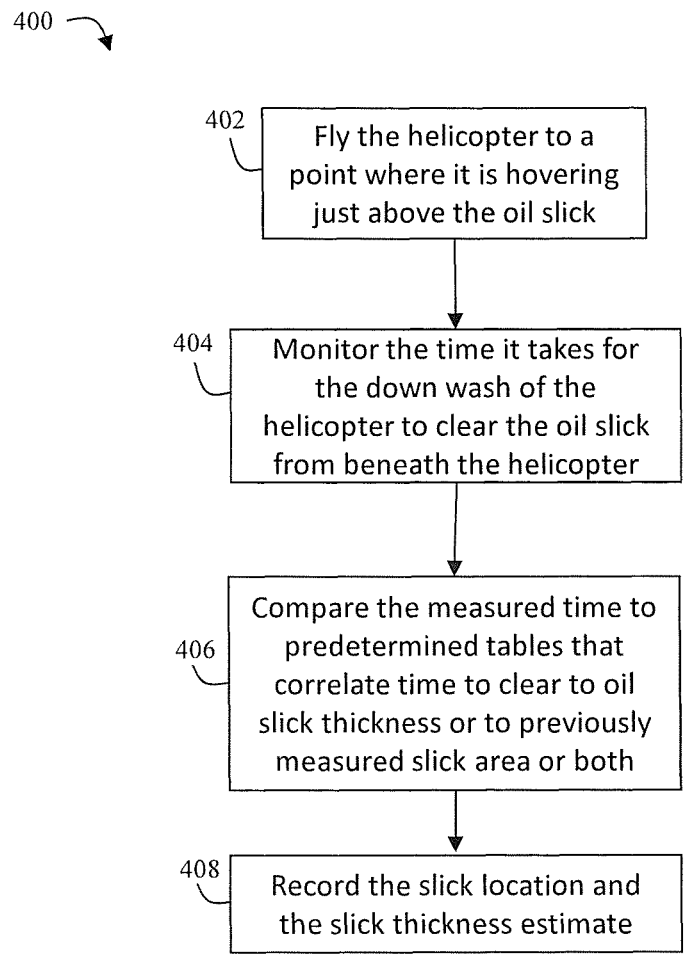
FIGS. 4 to 10 are flow charts for different methods of performing measurements with an airborne detection device in accordance with an exemplary embodiment of the present techniques.

In particular, FIG. 4 is a flow chart 400 for a first method of performing measurements with an airborne detection device in accordance with an exemplary embodiment of the present techniques. This method involves hovering over the oil slick and measuring the amount of time it takes the down wash to clear the area under it. The clearing time should correlate to slick thickness, which may be compared to predetermined tables that correlate clearing time to slick thickness. Alternately, the helicopter could use the down wash to quickly determine thick and thin areas by monitoring clearing time of different areas of the slick and comparing relative differences in clearing time. It is expected that thicker area clear more slowly than thinner areas. Once thicker areas are determined. The helicopter could deploy one or more thickness measurement components to more accurately determine slick thickness at desired locations based on the down wash measurements.

The process begins by flying the helicopter to a point where it is hovering just above the oil slick, as shown in block 402. The hovering height from the oil slick may be two feet, five feet, ten feet or more. Then, at block 404, the time it takes for the down wash of the helicopter to clear the oil slick from beneath the helicopter is monitored. The monitoring may include recording the clearing time and the associated location. Once the clearing time has been obtained, the measured clearing time is compared to predetermined tables that correlates clearing time to oil slick thickness or compared to clearing time of previously measure slicks or slick areas, as shown in block 406. The comparison may be performed by processor executing a set of instructions on the command unit and/or module associated with the helicopter. At block 408, the oil slick location and the oil slick thickness estimate is recorded. This record may be stored in memory in the command unit and/or a module associated with the helicopter.

Figure 5:
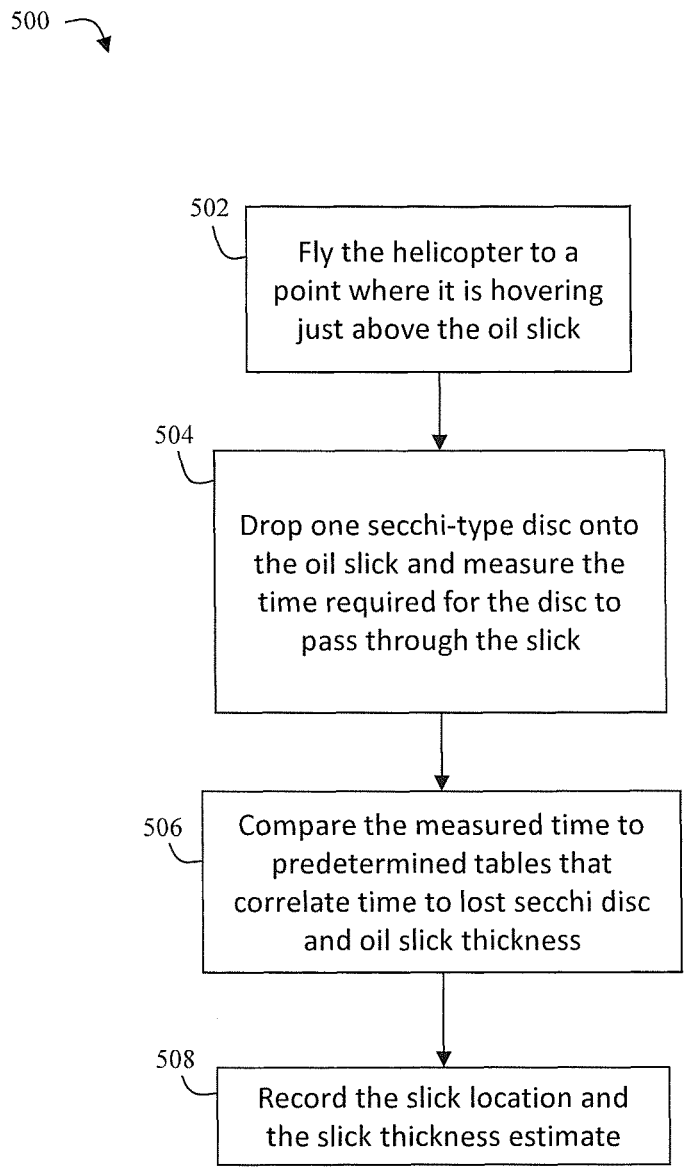

FIG. 5 is a flow chart 500 for a second method of performing measurements with an airborne detection device in accordance with an exemplary embodiment of the present techniques. This method may include loading the helicopter with sets of single-use Secchi-type disks (or similar visible objects) that can be released as the helicopter hovers over the slick. The disks may be release over the oil slick and the amount of time required for the helicopter HD/IR cameras to lose sight of the disk may be measured. Then, similar to the previous method, the time is compared to predetermined tables that correlate this time to slick thickness.

The process begins by flying the helicopter to a point where it is hovering just above the oil slick, as shown in block 502. The hovering height from the oil slick may be two feet, five feet, ten feet or more. Then, at block 504, one Secchi-type disc is dropped onto the oil slick and the time required for the disc to pass through the slick is measured. The monitoring may include recording the time for the Secchi-type disc to pass through the oil slick and no longer be visible. Once the drop time has been obtained, the measured drop time is compared to predetermined tables that correlate drop time to oil slick thickness, as shown in block 506. The comparison may be performed by a processor executing a set of instructions on the command unit and/or a module associated with the helicopter. At block 508, the oil slick location and the oil slick thickness estimate is recorded. This recordation may be stored in memory in the command unit and/or a module associated with the helicopter.

Figure 6:
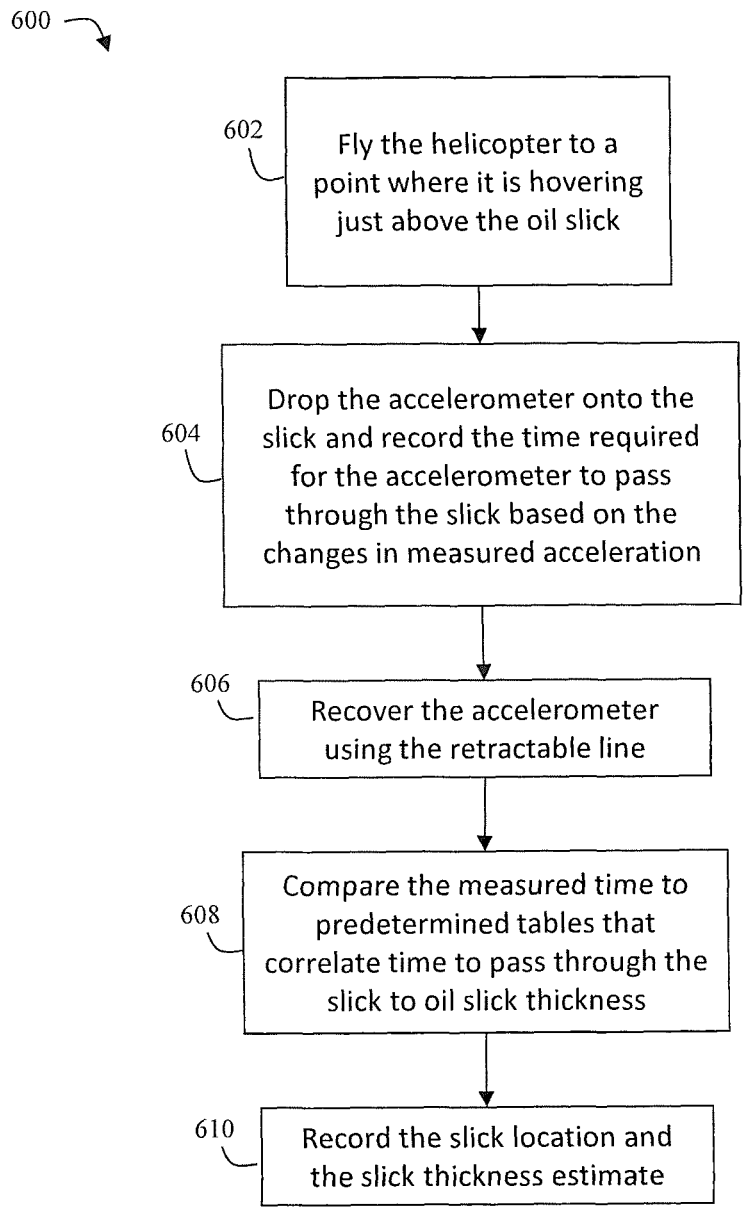

FIG. 6 is a flow chart 600 for a third method of performing measurements with an airborne detection device in accordance with an exemplary embodiment of the present techniques. This method utilizes an accelerometer attached to a retractable line on the helicopter. The accelerometer is dropped into the oil slick and via the acceleration signal, the amount of time required for the accelerometer to pass through the oil slick is measured. Then, the time is compared to predetermined tables that correlate this time to oil slick thickness.

The process begins by flying the helicopter to a point where it is hovering just above the oil slick, as shown in block 602. The hovering height from the oil slick may be two feet, five feet, ten feet or more. Then, at block 604, the accelerometer is dropped into the oil slick and the time required for the accelerometer to pass through the oil slick based on the changes in measured acceleration is recorded. Then, the accelerometer is recovered using the retractable line, as shown in block 606. The measured time is compared to predetermined tables that correlate measured time to oil slick thickness, as shown in block 608. The comparison may be performed by a processor executing a set of instructions on the command unit and/or module associated with the helicopter. At block 610, the oil slick location and the oil slick thickness estimate is recorded. This record may be stored in memory in the command unit and/or a module associated with the helicopter.

Figure 7:
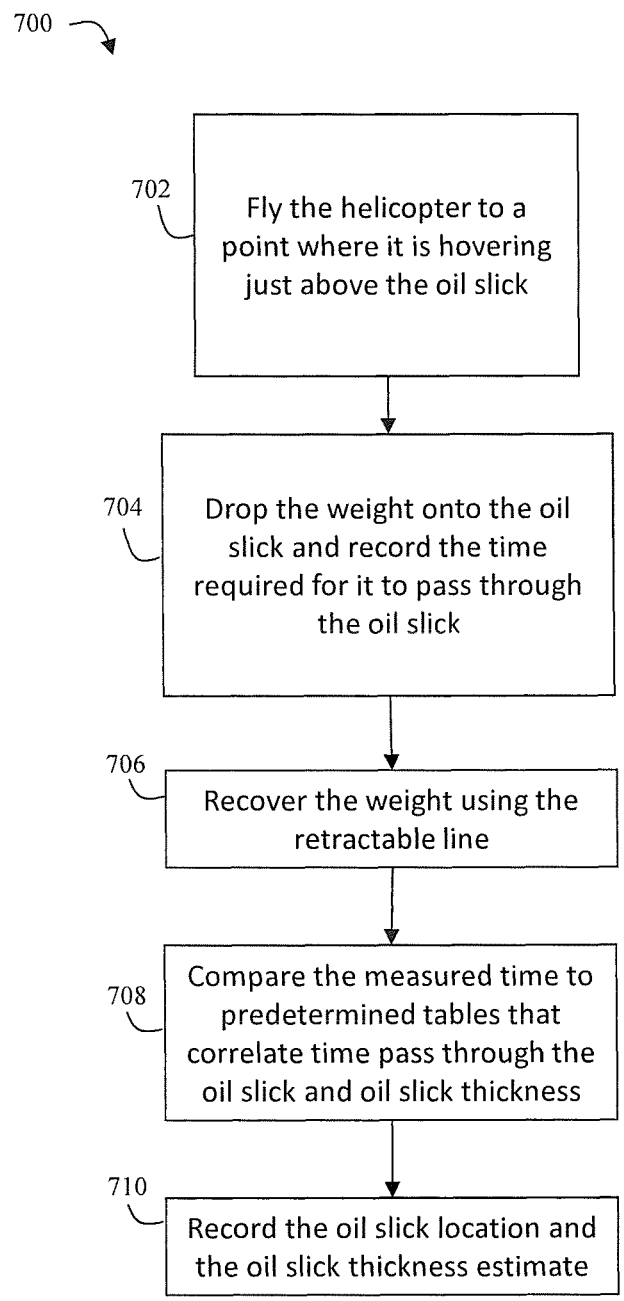

FIG. 7 is a flow chart 700 for a fourth method of performing measurements with an airborne detection device in accordance with an exemplary embodiment of the present techniques. This method involves placing a small visible weight attached to a retractable line on the helicopter. The weight is dropped into the oil slick and measure the amount of time for it to pass through the oil slick based on the loss of visibility as measure by the HD/IR cameras. Then, the time is compared to predetermined tables that correlate this time to slick thickness.

The process begins by flying the helicopter to a point where it is hovering just above the oil slick, as shown in block 702. The hovering height from the oil slick may be two feet, five feet, ten feet or more. Then, at block 704, the weight is dropped into the oil slick and the time required for the weight to pass through the oil slick is measured and is recorded. Then, the weight is recovered using the retractable line, as shown in block 706. Once the weight has been obtained, the measured time is compared to predetermined tables that correlate measured time to oil slick thickness, as shown in block 708. The comparison may be performed by a processor executing a set of instructions on the command unit and/or a module associated with the helicopter. At block 710, the oil slick location and the oil slick thickness estimate is recorded. This record may be stored in memory in the command unit and/or a module associated with the helicopter.

Figure 8:
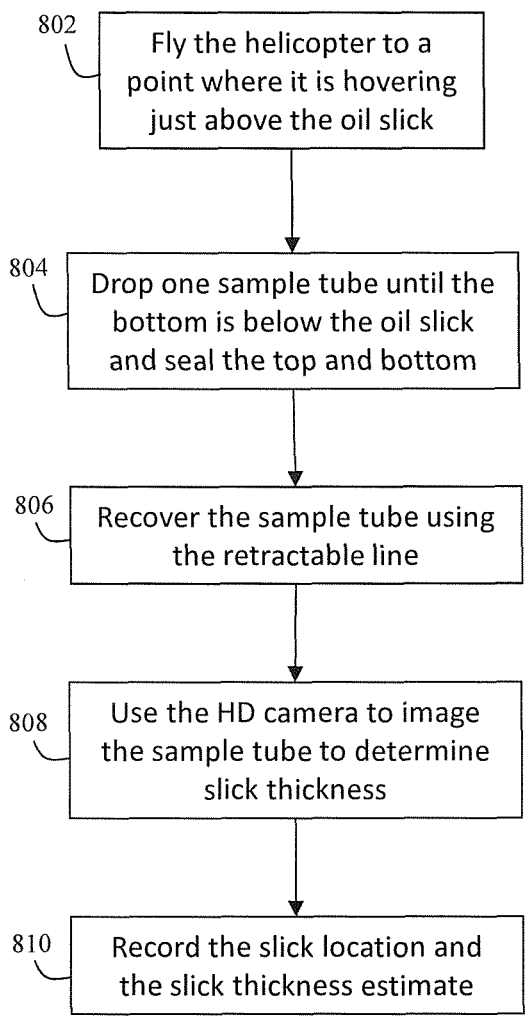

FIG. 8 is a flow chart 800 for a fifth method of performing measurements with an airborne detection device in accordance with an exemplary embodiment of the present techniques. This method places one or more clear sample tube attached to a retractable line on the helicopter. The sample tube/s are open at each end, but the ends can be closed remotely to seal the tube. The helicopter may hover at an appropriate distance above the oil slick to avoid having the helicopter down wash disturb the slick thickness. The sample tube is lowered until it is at least partly passing through the oil slick and the bottom is located in the water below the oil slick and the top is located above the oil slick (e.g., in the air above the oil slick). This could be facilitated by placing the tube in a buoyancy device that causes it to float in the proper location. At this point, both ends of the sample tube are closed and the tub returned to the helicopter using the retractable line. Once at the helicopter, an image is taken of the tube using the HD camera to determine slick thickness.

The process begins by flying the helicopter to a point where it is hovering just above the oil slick, as shown in block 802. The hovering height from the oil slick may be twenty feet, thirty feet or more to prevent the down wash from disturbing the oil slick. Then, at block 804, the sample tube is lowered until it is at least partly passing through the oil slick and the bottom is located in the water below the oil slick and the top is located above the oil slick (e.g., in the air above the oil slick). The tube may be placed in a buoyancy device that causes it to float in the proper location. Then, the sample tube is recovered using the retractable line, as shown in block 806. Once the sample tube has been obtained, the HD camera may be used to image the sample tube to determine slick thickness, as shown in block 808. At block 810, the oil slick location and the oil slick thickness estimate is recorded. This record may be stored in memory in the command unit and/or a module associated with the helicopter.

Figure 9:
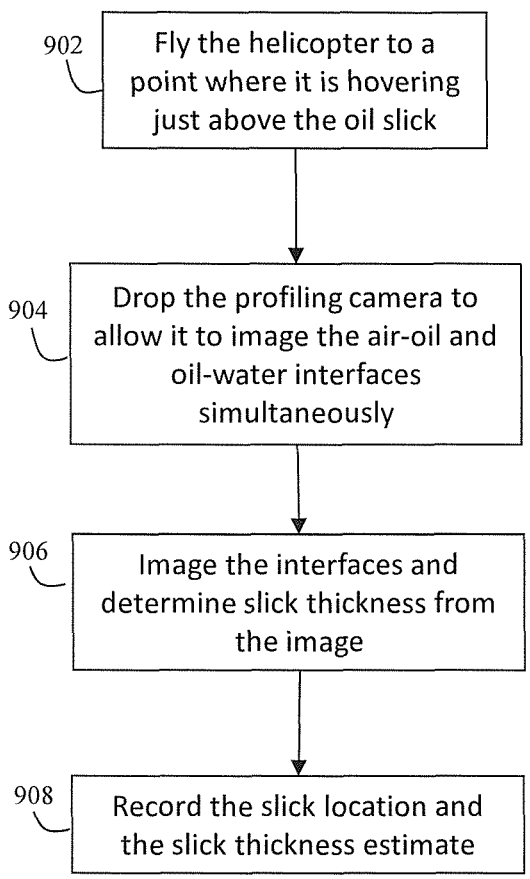

FIG. 9 is a flow chart 900 for a sixth method of performing measurements with an airborne detection device in accordance with an exemplary embodiment of the present techniques. This method involves placing an imaging camera attached to a retractable line on the helicopter. The camera is set up in a configuration to photograph a profile of the air-oil-water interfaces. It is also set up in a configuration that allows the lens to be cleared of oil between sampling and/or imaging at the different locations. The helicopter hovers an appropriate distance above the oil slick to avoid having the helicopter down wash disturb the slick thickness. The camera is lowered into the oil slick so that the lens can image the air-oil and oil-water interface simultaneously. This could be facilitated by placing the camera in a buoyancy device that causes it to float in the proper location. Then, the oil slick thickness is determined based on the images.

The process begins by flying the helicopter to a point where it is hovering just above the oil slick, as shown in block 902. The hovering height from the oil slick may be twenty feet, thirty feet or more to prevent the down wash from disturbing the oil slick. Then, at block 904, the camera, which may be in a flotation device, is lowered until it is at least partly passing through the oil slick, such that the camera may capture the air-oil and oil-water interface simultaneously. Then, the camera is recovered using the retractable line. Once the camera image has been obtained, the image may be used to determine the oil slick thickness, as shown in block 906. At block 908, the oil slick location and the oil slick thickness estimate is recorded. This record may be stored in memory in the command unit and/or a module associated with the helicopter.

Figure 10:
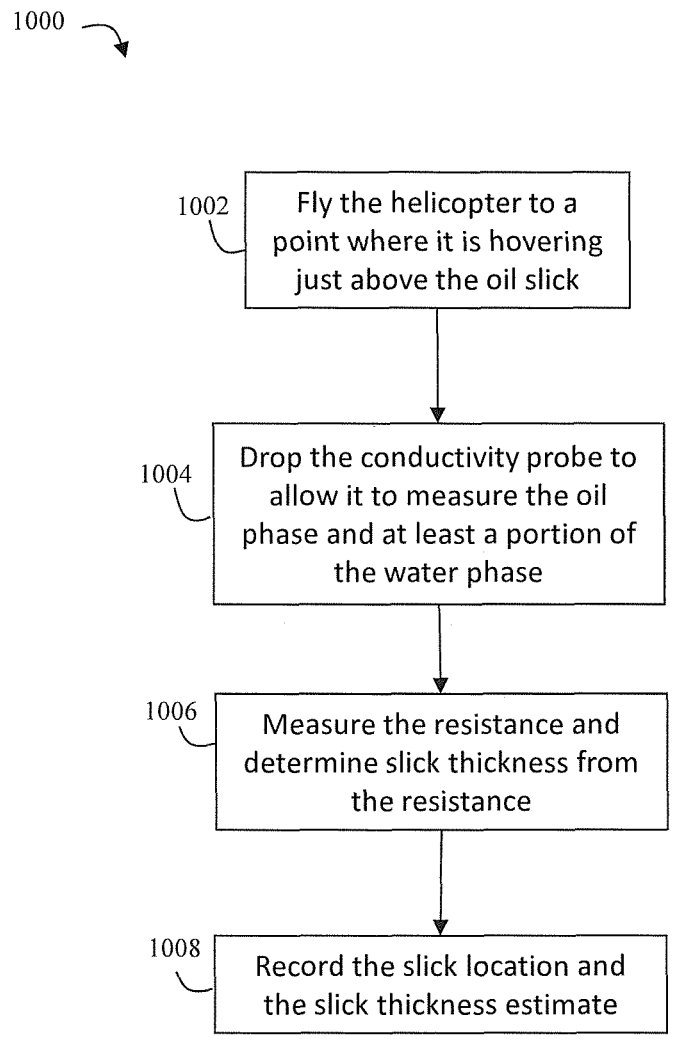

FIG. 10 is a flow chart 1000 for a seventh method of performing measurements with an airborne detection device in accordance with an exemplary embodiment of the present techniques. This method involves placing a conductivity probe attached to a retractable line on the helicopter. The helicopter hovers an appropriate distance above the oil slick to avoid having the helicopter down wash disturb the slick thickness. The conductivity probe is lowered into the oil slick so that the resistance of the oil-water phase for a specific distance, e.g., 0.1 centimeters (cm), 0.5 cm, 1.0 cm, or more, is measured. This could be facilitated by placing the conductivity probe in a buoyancy device that causes it to float in the proper location. Then, the oil slick thickness is determined based on the measured resistance by comparing this resistance to tables that correlate resistance to slick thickness.

The process begins by flying the helicopter to a point where it is hovering just above the oil slick, as shown in block 1002. The hovering height from the oil slick may be twenty feet, thirty feet or more to prevent the down wash from disturbing the oil slick. Then, at block 1004, the conductivity probe, which may be in a flotation device, is lowered until it is at least partly passing through the oil slick, such that the conductivity probe may measure the resistance of the oil phase and at least a portion of the water phase. Then, the conductivity probe is recovered using the retractable line. The measure resistance may be used to determine the oil slick thickness, by comparing it tables that correlate resistance to slick thickness, as shown in block 1006. At block 1008, the oil slick location and the oil slick thickness estimate is recorded. This record may be stored in memory in the command unit and/or a module associated with the helicopter.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

The invention claimed is:

1. A method for managing an oil release with one or more airborne devices, comprising:
   deploying a marine vessel having an airborne detection device to a location in a body of water near an oil slick;
   hovering the airborne detection device above the oil slick;
   measuring thickness of the oil slick at the location by contacting the oil slick with a measurement component deployed from the airborne detection device; and
   transmitting a signal associated with the thickness of the oil slick to a command unit, wherein the measurement component includes an imaging camera to contact the oil slick, and measuring the thickness further includes capturing an image of an air-oil interface and an oil-water interface, and retracting the imaging camera out of the oil slick.

2. The method of claim 1, comprising determining a response technique based at least partially on the thickness of the oil slick.

3. The method of claim 1, further comprising programming the airborne detection device to be able to communicate with the command unit prior to hovering the airborne detection device.

4. The method of claim 1, wherein the signal is transmitted to the command unit when a thickness measurement has been obtained.

5. The method of claim 1 further comprising receiving the signal at the command unit; extracting a measured thickness image from the signal; and displaying the measured thickness image on a monitor.

6. The method of claim 1, further comprising deploying a response team to treat the oil slick based upon the measured thickness of the oil slick.

7. The method of claim 1, wherein the imaging camera is a high definition camera.

8. The method of claim 1, wherein the thickness of the oil slick is measured in multiple areas of the oil slick.

9. The method of claim 1, further comprising identifying the oil slick using an additional camera.

10. The method of claim 9, wherein the additional camera is a high definition camera.

11. The method of claim 9, wherein the additional camera is an infrared camera.

12. The method of claim 1, wherein the measuring component includes a buoyancy device into which the imaging camera is placed such that the imaging camera captures the image of the air-oil interface and the oil-water interface.

13. A hydrocarbon release management system comprising:
a command unit; and
an airborne detection device in communication with the command unit and having a propulsion component, a communication component, and a measurement component, wherein the propulsion component is configured to maneuver the airborne detection device, the measurement component is configured to measure the thickness of the oil slick by contacting the oil slick with the measurement component deployed from the airborne detection device, and the communication component is configured to communicate signals associated with the measured thickness to the command unit wherein the measurement component comprises a camera attached to a retractable line.

14. The system of claim 13, wherein the airborne detection device is configured to be controlled via remote control communications.

15. The system of claim 13, wherein the airborne detection device further includes a power component that is configured to provide power to one or more of the measurement component and the communication component.

16. The system of claim 13, wherein the communication component is configured to transmit to the command unit via one or more of wireless communication hardware and cellular communication hardware.

17. The system of claim 13, wherein the camera is a high definition camera.

18. The system of claim 13, wherein the command unit is a computer system comprising:
a processor;
memory in communication with the processor; and
a set of instructions stored on the memory and accessible by the processor, wherein the set of instructions, when executed, are configured to:
receive the transmitted signal from the airborne detection device;
determine the thickness of the oil slick based on the transmitted signal; and
provide a visible indication of the thickness of the oil slick based on the determination.

19. The system of claim 18, wherein the determination of the thickness of the oil slick based on the transmitted signal comprises a set of instructions, when executed, configured to display an image on a monitor to determine the thickness of the oil slick based on the image.

20. The system of claim 18, further comprising a set of instructions stored on the memory and accessible by the processor, wherein the set of instructions, when executed, are configured to provide one or more of a visual indication and audible notification associated with the thickness of the oil slick.

21. The system of claim 18, further comprising a set of instructions stored on the memory and accessible by the processor, wherein the set of instructions, when executed, are configured to store the thickness of the oil slick at the specific location.

22. The system of claim 13, wherein the camera is a high definition camera.

23. The system of claim 13, further comprising an additional camera to initially identify the oil slick.

24. The system of claim 23, wherein the additional camera is a high definition camera.

25. The system of claim 23, wherein the additional camera is an infrared camera.

26. The system of claim 13, wherein the measuring component includes a buoyancy device into which the camera is placed such that the camera captures an image of an air-oil interface and an oil-water interface when contacting the oil slick.

* * * * *